United States Patent [19]
Gschwind et al.

[11] Patent Number: 5,568,977
[45] Date of Patent: Oct. 29, 1996

[54] PROCESS AND DEVICE TO DETECT A RISK OF WATER CONDENSATION ON A SURFACE BEING IN CONTACT WITH A WET AIR VOLUME

[75] Inventors: Michel Gschwind, Grasse; Pascal Ancey, Le Rouret, both of France

[73] Assignee: Imra Europe SA, Valbonne, France

[21] Appl. No.: 191,048

[22] Filed: Feb. 3, 1994

[30] Foreign Application Priority Data

Feb. 24, 1993 [FR] France ................ 93 02099

[51] Int. Cl.$^6$ ................ G01N 25/12; G01N 25/68
[52] U.S. Cl. ................ 374/45; 374/54; 374/28
[58] Field of Search ................ 374/45, 54, 27, 374/28

[56] References Cited

U.S. PATENT DOCUMENTS

| | | | |
|---|---|---|---|
| 3,284,003 | 11/1966 | Ciemochowski | 374/28 |
| 3,287,974 | 11/1966 | Ciemochowski | 374/28 |
| 3,396,574 | 8/1968 | Hanlein et al. | 374/28 |
| 4,240,284 | 12/1980 | Nguyen . | |
| 4,435,091 | 3/1984 | Nedreski | 374/20 |
| 4,579,462 | 4/1986 | Rall et al. | 374/16 |
| 4,946,288 | 8/1990 | Siska et al. | 374/28 |
| 5,139,344 | 8/1992 | Mutter | 374/28 |

FOREIGN PATENT DOCUMENTS

| | | | |
|---|---|---|---|
| 61-138193 | 6/1986 | Japan | 374/28 |
| 404128643 | 4/1992 | Japan | 374/28 |
| 2036339 | 6/1980 | United Kingdom . | |
| 2190203 | 11/1987 | United Kingdom | 374/28 |
| 9218854 | 10/1992 | WIPO . | |

Primary Examiner—Diego F. F. Gutierrez
Attorney, Agent, or Firm—Foley & Lardner

[57] ABSTRACT

A process is disclosed to detect a water condensation risk on a surface in contact with a wet air volume, which uses the steps of (a) placing a sensitive element on the surface, which initially takes a temperature corresponding to that of the surface, (b) by means of a heating device on this sensitive element, initiating a first heating phase until a temperature higher than the surface temperature is reached, (c) by means of a cooling device having the same thermal power as the heating device, initiating a cooling phase until a temperature lower than the surface temperature is provoked on the sensitive element, and (d) a comparison is made between the ratio of the first heating phase time to the temperature rise during heating and the ratio of cooling phase time to the temperature decrease during the cooling, a noticeable difference between these two ratios indicating a significant risk of condensation on the surface.

11 Claims, 6 Drawing Sheets

PROCESS AND DEVICE TO DETECT A RISK OF WATER CONDENSATION ON A SURFACE BEING IN CONTACT WITH A WET AIR VOLUME

BACKGROUND OF THE INVENTION

1. Field of the Invention

The present invention concerns a process to detect a water condensation risk on a surface in contact with a wet air volume, and a device to implement this process.

2. Description of the Related Art

It is known that, the water steam condensation phenomenon on a surface in particular results from a temperature decrease of the surface or from an increase in the water steam quantity present in the air.

It is worthwhile to be able to detect in advance a condensation risk in many situations, like for instance on the glass surfaces of a green house, of a house, a road vehicle or in other domains without any limitation.

Devices allowing detection of the preliminary conditions of water condensation on surfaces are already known.

Such devices usually resort to hygrometric or thermometric sensors which don't always have satisfactory accuracy and reliability.

SUMMARY OF THE INVENTION

The present invention aims at providing a new process allowing detection with a high reliability, and in an especially simple way, the conditions preceding water condensation formation on a surface.

The process according to the invention can be applied to a condensation risk detection on the surface of any object placed in a wet air volume.

In particular, if the object surface temperature is similar to that of the wet air, the detection of a condensation risk may allow to detect the wet air volume dew-point.

DESCRIPTION OF PREFERRED EMBODIMENTS

Figure 1:
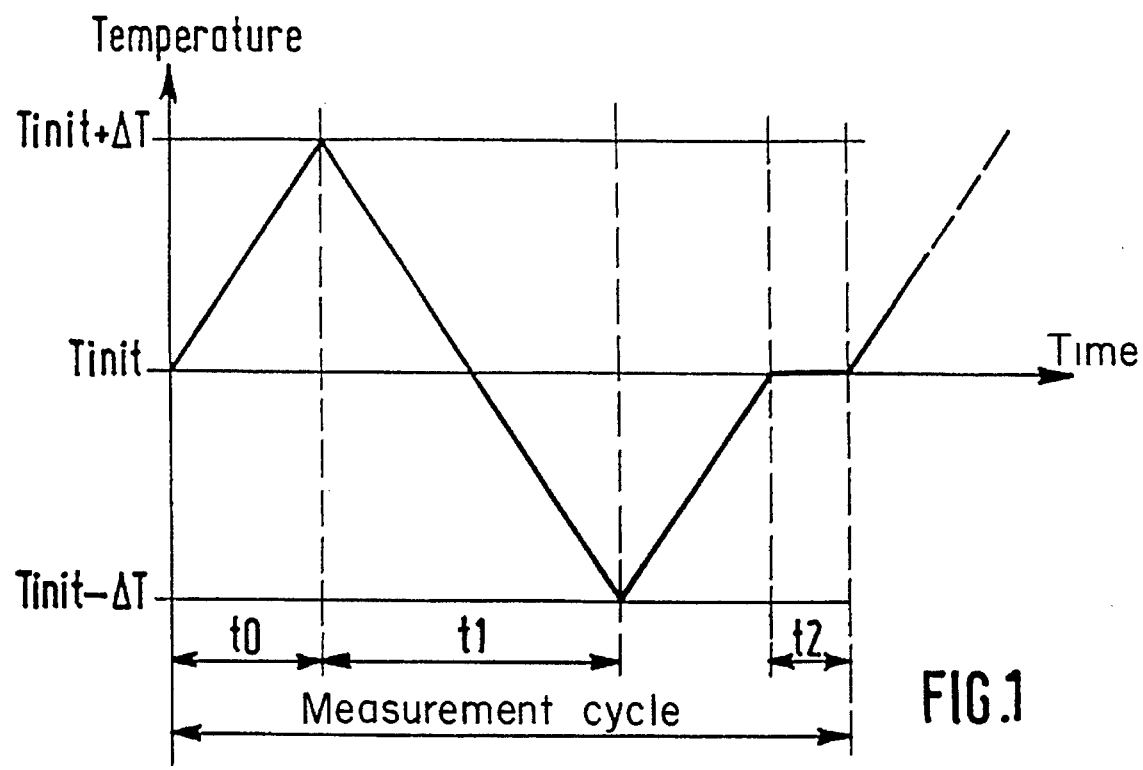
FIG. 1 shows temperature change over time of the sensitive element where there is no condensation while cooling during the first implementation mode.

The present invention aims at a process to detect a water condensation risk on a surface in contact with a wet air volume, characterized by the fact that the following steps are realized:

a) a sensitive element is provided on the surface and it initially takes a temperature corresponding to the surface temperature, b) on this sensitive element, a first heating phase is caused with a heating device until a temperature higher than surface temperature is reached, c) on this sensitive element, a cooling phase is provoked by means of a cooling device having the same thermal power as the heating device until a temperature lower than surface temperature is reached, d) a comparison is made between the ratio of the first heating phase duration to the temperature raise during heating and the ratio of cooling phase to the temperature decrease while cooling, a noticeable difference between these two ratios being significant of a condensation risk on the surface.

According to the invention, the existence of a difference between the two ratios, one related to the first heating phase, the other to the cooling phase, indicates that there is a condensation on the sensitive element during cooling.

Indeed, the energy required to cool down and condense some steam quantity, for a given temperature difference, is greater than the energy required to heat up the same steam quantity with a similar temperature difference, but without state change.

But since the heating and cooling means have the same thermal power, this energy gap is expressed by a time gap between the heating phase and the cooling phase.

In a preferred implementation mode of the invention, the high temperature corresponding to the sensitive element temperature at the end of the first heating phase, as well as the low temperature corresponding to the sensitive element temperature at the end of the cooling phase, are set in advance.

It is understandable that the choice of a large temperature difference leads to a very early condensation risk detection on the surface.

On the other hand, if a relatively small temperature difference is chosen, the condensation risk is detected with a very short advance compared with the moment when condensation is actually appearing on the surface.

Preferably, according to this implementation mode, high and low temperatures are selected so that the sensitive element temperature variations have a symmetrical amplitude compared to the surface temperature (Tinit).

In other words, high and low temperatures are set by adding, and respectively subtracting, a ΔT predetermined temperature difference at the surface Tinit temperature.

In this case, if the first heating step consists in raising the sensitive element temperature from the Tinit value to the Tinit+ΔT value, and if the cooling phase consists in decreasing the sensitive element temperature from the Tinit+ΔT value to Tinit−ΔT value, the tc duration of the first heating phase must be equivalent to half of the tf duration of the cooling phase.

In the opposite case, that is to say if the cooling time tf is twice higher than the tc heating time, there must have been condensation while cooling down, which means that condensation risk on the surface is important.

In one preferred embodiment, the sensitive element absolute temperature is not measured, and only the temperature variations, that is to say +ΔT while heating and −2 ΔT while cooling, are measured.

This embodiment is particularly interesting since measuring tools provide parameters, especially electrical, which are characteristic of the sensitive element temperature variations. Thus it is useless to calibrate the measuring tools used.

In a preferential embodiment of the invention, after the cooling phase, a second heating phase of the sensitive element by means of the heating device is carried out in order to bring back the temperature of the said sensitive element to the level it had before the cooling phase.

Thus the sensitive element can be submitted to a series of thermal cycles, each of them made of a cooling phase and of a second heating phase.

Without condensation, the total cycle duration is almost equivalent to four times the first heating phase duration, whereas in case of condensation, the cooling phase and the second heating phase have respectively an extended duration.

A variation in the execution of the process is to then compare the first heating phase duration to the quarter of the total duration of such a cycle, and to submit the sensitive element to successive cycles, until this duration becomes longer than the first heating phase. Then there is a condensation risk.

One can notice that, in this case, sensitivity is better because the condensation while cooling down as well as the evaporation while heating are taken into account.

Furthermore, in this variation, measurement of the first heating phase duration is made only once, to be used later during successive cycles.

According to another variation, one could record the total duration of a cycle, of which the fact that it provoked no condensation is well known, and compare the duration of later cycles to this recorded duration.

According to a specific embodiment, the cycles succession is regularly interrupted by a resting phase during which neither the sensitive element nor the surface is submitted to any heating or cooling from the heating or cooling device, so that they recover a stable temperature according to the environmental conditions, before being again submitted, first to a heating phase, then to successive thermal cycles.

According to the invention, it is better that the surface, on which detection will be carried out, possess a thermal time constant bigger than that of the sensitive element. Thus the different temperature cycles applied to the sensitive element alter only insignificantly the surface temperature.

If this condition was not verified, the zone of the surface nearing the sensitive element would be submitted to thermal oscillations of the same amplitude as those of the sensitive element.

It is also possible to implement the invention by replacing the cooling phase by the second heating phase.

In that case, the comparison is made between the ratio of the first heating phase duration to the temperature raise during the first heating phase and the ratio of the second heating phase to the temperature raise during the second heating phase.

Then, the thermal power of the cooling device does not matter and has no influence on the validity of the comparison.

In this embodiment, it is worthwhile to compare the whole duration of a cycle to that of a former cycle which provoked no condensation.

In a preferred embodiment of the invention, a Peltier effect module is used as a sensitive element and as heating and cooling devices.

One of the Peltier effect module faces is applied against the surface, on which the detection of a condensation risk is sought.

The other face of the Peltier effect module, in contact with the air, is used as a sensitive element.

Then, only by inverting the direction of the supply power of the Peltier effect module, it is possible to cool down or heat up its face used as a sensitive element.

Furthermore, the temperature variations of the Peltier effect module can be continuously determined by measuring the voltage at the terminals of the Peltier effect module.

Consequently, the use of a Peltier effect module is particularly fit to execute the preferred embodiment of the invention, in which no characteristic rang of the sensitive element absolute temperature is measured, but only characteristic ranges of the temperature differences between this sensitive element and the surface.

It is indeed known that the voltage at the terminals of a Peltier effect module, fed by a given current, includes a resistive component resulting from the internal resistance of the said Peltier effect module, and a component induced by the difference of temperature between the two faces of the module. This induced component, due to the Seebeck effect, is designated as Seebeck component.

The measure of this Seebeck component allows one to follow the temperature variations of the Peltier effect module.

The Seebeck component of voltage at the terminals of the Peltier effect module can be obtained by eliminating a constant component representative of the voltage due to the internal resistance of the Peltier effect module at constant temperature in the voltage at the terminals of the Peltier effect module. Also, the Seebeck component of voltage at the terminals of the Peltier effect module can be obtained by eliminating a variable component due to the internal resistance of the Peltier effect module at the average temperature of the Peltier effect module in the voltage at its terminals.

It is thus sufficient to isolate this Seebeck component by subtracting the component resistive to the voltage signal at the terminals of the Peltier effect module, and to compare its amplitude to predetermined high and low voltage values, to detect at which moment of the cycle the Peltier effect module face, used as a sensitive element, shows a given temperature gap compared with the surface.

According to a preferred variation, the whole of the resistive component is subtracted, that is the resistive component taken at the surface initial temperature, as well as the variations of this resistive component, due to the Peltier effect module's temperature changes.

The determination of the sensitive element temperature changes by measuring the voltage at the terminals of the Peltier effect module is particularly reliable since it does not require any thermometric sensor, which may alter the measurement.

The present invention also is directed to a device to implement the above described process, characterized by the fact that it includes: a sensitive element, that can be applied against the surface and can have a temperature almost similar to that of the surface, a heating and a cooling devices able to respectively heat and cool the said sensitive element, a measurement device of the sensitive element temperature, a comparator of the sensitive element temperature with high and low values set in advance, a control that releases at least a first heating phase until the sensitive element temperature reaches the high value, then a cooling phase until the sensitive element temperature reaches the low value, a clock to measure the heating and the cooling phases duration and a comparator to compare the ratio of heating time to temperature raise during heating and the ratio of cooling time to temperature decrease during cooling, the comparator warning of the condensation risk in case of noticeable difference between these two ratios.

In a preferred embodiment, the appliance includes, as a sensitive element, as a cooling device and as a heating device, a Peltier effect module.

In this case, an electronic circuit helps to control the supply of the Peltier effect module.

This electronic circuit is determining the durations of the heating and cooling phases by comparing the amplitude of the Seebeck component of the voltage present at the terminals of the Peltier effect module, resulting from the temperature differences between the two faces of the Peltier effect module, with preset high and low voltage values.

In order to better explain the invention, we are going to describe now two specific implementation modes as well as two specific embodiments, given as examples and without any restrictive character.

Figure 2:
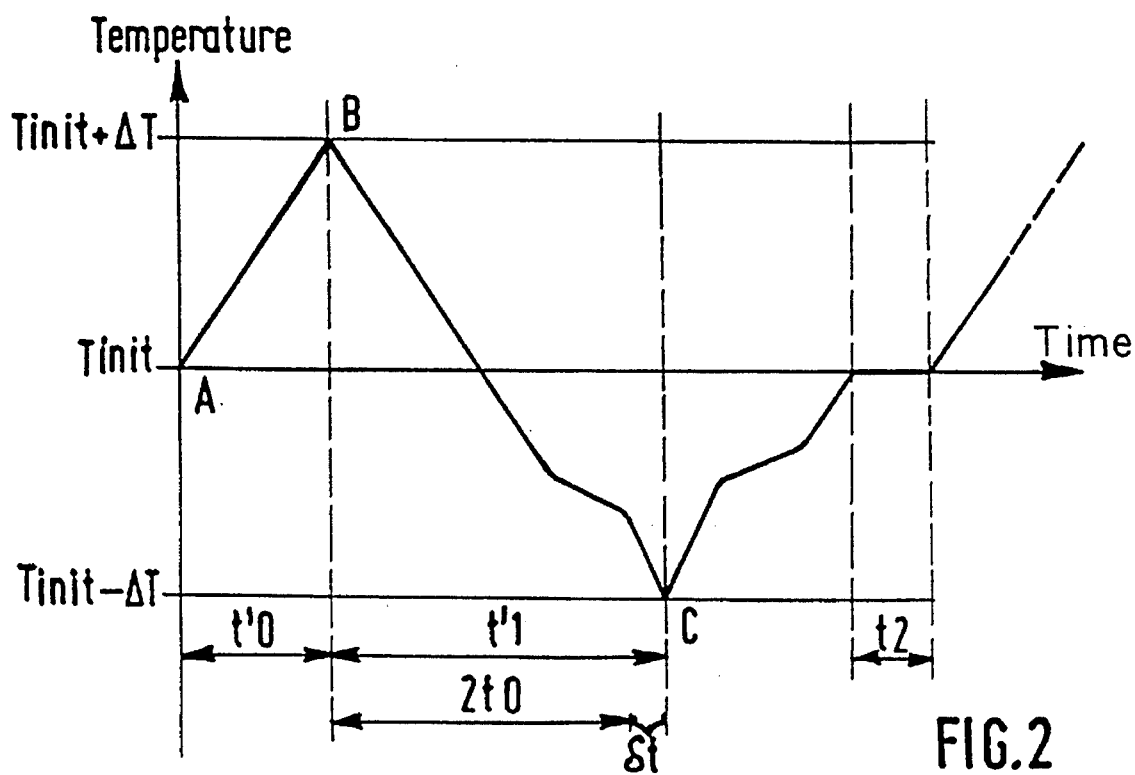
FIG. 2 shows temperature change over time of the sensitive element where there is a temperature stage corresponding to the water condensation phase during the first implementation mode.

In FIGS. 1 and 2, the Tinit value represents the initial temperature of the sensitive element, that is the temperature of the surface on which ones wants to detect a condensation risk.

According to a particular implementation of the invention process, we have predetermined the maximum value and the minimum value of the thermal variations by respectively adding and subtracting a $\Delta T$ temperature gap to the Tinit value.

The first heating phase is spreading over a $t_0$ period, and the thermal cycle includes a cooling phase spreading over a $t_1$ period, as well as a second heating phase interrupted by a resting phase spreading over a $t_2$ period.

The temperature raise during the first heating is of $\Delta T$, the temperature decrease during cooling is of $2\Delta T$.

Consequently, in the case of FIG. 1 where there is no condensation while cooling, the $t_1$ cooling time is almost equal to 2 times the duration of the first $t_0$ heating phase.

On the other hand, on the FIG. 2, we clearly see a temperature stage corresponding to the liquid water steam condensation phase.

This temperature stage, which cannot be directly measured in the present invention process, is shown by the fact that the cooling time $t'_1$ shows a $\delta t$ gap with twice the to heating time.

Schematically, if we call A, B, C the points of the respective coordinates (0, Tinit), ($t_0$, Tinit+$\Delta T$), ($t_0+t'_1$, Tinit-$\Delta T$) on the FIG. 2, the process according to the invention consists in comparing the absolute value of the slope of the straight line AB to that of the straight line BC.

Even though the $t_2$ resting phase has been represented during the second heating phases on the FIGS. 1 and 2, such a resting phase could appear only periodically.

Without this resting phase, the second heating phase has a duration equal to that of the cooling phase.

Consequently, each cycle has a duration respectively equivalent to 2 $t_1$, 2$t'_1$, and it should be possible, according to a variation of the invention implementation, to compare to to a quarter of the cycle total duration.

Figure 3:
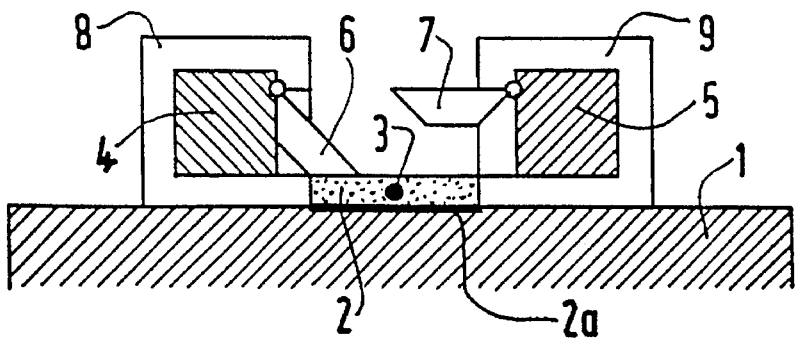
FIG. 3 is a block diagram of the device for implementing the process of the present invention.

The FIG. 3 is schematically representing a device allowing an implementation of the process which has just been described.

On a surface 1, a sensitive element 2 made in a material having a very high thermal conductivity is placed so as to tightly adhere to the surface 1, for instance by means of a heat conducting fixing agent 2a.

Inside the sensitive element 2, a thermometric sensor 3 supplies an electric signal representative of the temperature of the said sensitive element 2.

On either side of the sensitive element 2, there is a cold source 4 and a hot source 5 that can each exchange thermal energy with sensitive element 2, through heat conductors 6 and 7 able to alternately get in contact with the sensitive element 2. On the FIG. 3, the heat conductor 6 is carrying thermal energy between the sensitive element 2 and the cold source 4.

Insulating boxes 8 and 9 prevent any thermal energy transfer between the cold source 4 and hot source 5, on the one hand, and the surface 1 or the outside on the other hand.

Figure 4:
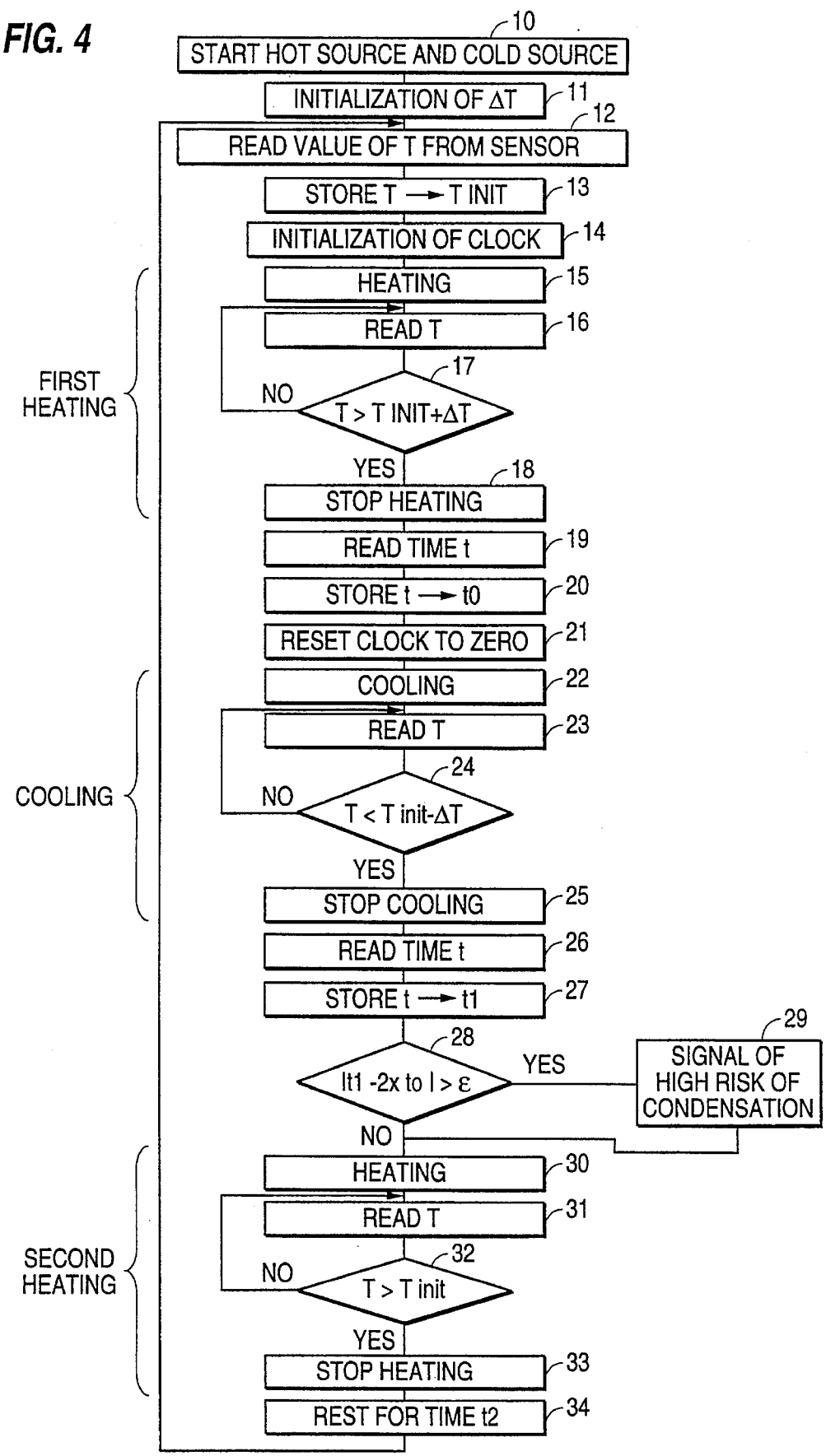
FIG. 4 is a flow chart of the steps of the first mode of the process of the present invention.

Operation of the FIG. 3 device follows the steps represented in FIG. 4.

After starting the cold source 4 and hot source 5, during a step 10, the $\Delta T$ value, characterizing the detection advance compared to the condensation phenomenon appearance, is chosen during a step 11.

The following step 12 is the sensitive element Tinit temperature measurement step, which is later on memorized at step 13.

At step 14, the heating time counting is started by a clock initialization.

At step 15, the sensitive element 2 is heated by contact with the heat conductor 7 of the hot source 5.

Steps 16 and 17 are a waiting loop until the temperature of sensitive element 2 reaches the Tinit+$\Delta T$ value.

At step 18, the heating is stopped, by withdrawal of heat conductor 7 from sensitive element 2.

The heating time to is measured and memorized at steps 19 and 20.

The clock is again initialized from step 21.

At step 22, the cooling of the sensitive element is started until it reaches the Tinit-$\Delta T$ temperature (steps 23 and 24). To that purpose, the heat conductor 6 is put in contact with sensitive element 2.

At following step 25, the cooling is stopped by withdrawing the thermal conductor 6 from the sensitive element 2 and at steps 26 and 27, the cooling time $T_1$ is read on the clock and memorized.

Step 28 is corresponding to the comparison between the cooling time $t_1$ and twice the heating time $t_0$.

$\epsilon$ represents the tolerable error of measure below which these two values are considered as equivalent.

In case of a difference between $t_1$ and $2t_0$ equivalent to $\epsilon$, the step 29, that indicates the release of an important condensation risk signal, is carried out.

In case of $\epsilon$ equality between $t_1$ and $2t_0$, the following step is carried out.

The sensitive element 2 is brought back to a temperature close to Tinit during the steps 30 to 33.

During the step 34, the sensitive element 2 and the surface 1 are not concerned for a $t_2$ duration by the thermal constraints of the hot and cold sources, so that they can recover a stable temperature according to the surrounding conditions.

In its optimal value, the duration $t_2$ is approximately equivalent to 5 times the system time constant.

The detection thermal cycle is reiterated by going back to step 21.

One can notice that it is not necessary to calibrate the thermometric sensor 3 since the only measurements to perform correspond to temperature variations.

Figure 6A:
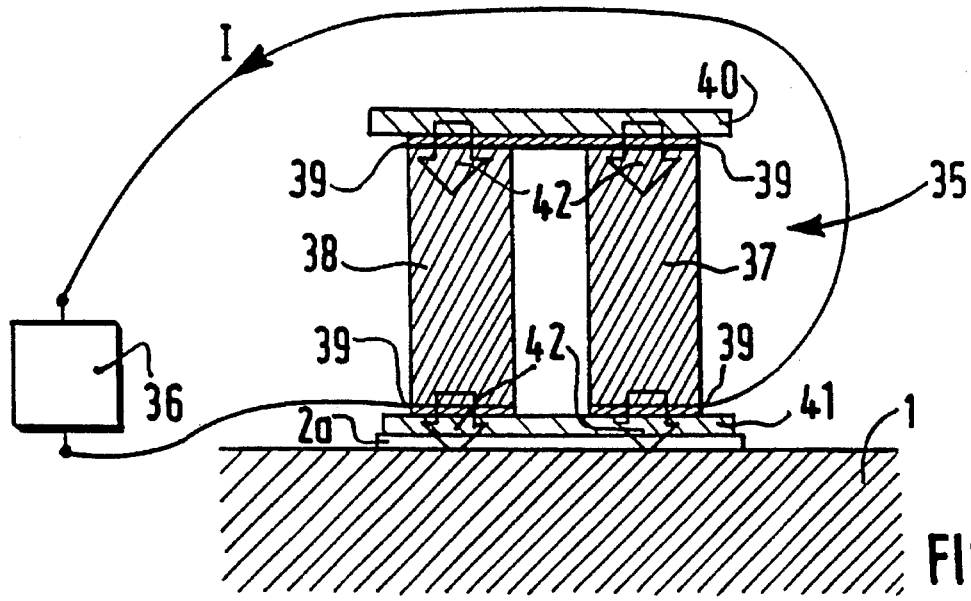
FIGS. 6a and 6b show a device for implementing the second implementation mode of the process of the present invention.
Figure 6B:
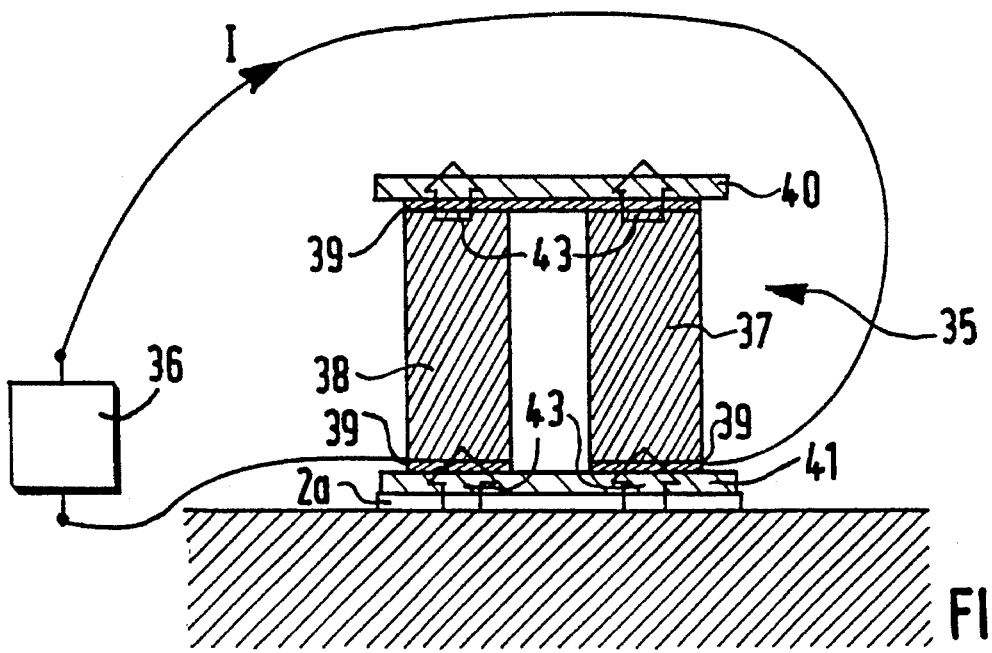

In FIGS. 6a and 6b, a device, according to another realization mode of the invention and that is carrying out a second implementation mode of the invention process, is represented.

In this device, the sensitive element 2, the thermometric sensor 3, as well as the cold source 4 and hot source 5 of FIG. 3 are replaced by a Peltier effect module 35.

An electronic circuit 36 supplies the necessary current I necessary for operation of module 35.

This last module is made of two semi-conductive elements 37 and 38 respectively doped N and P, that are electrically connected in series by electrodes 39 and hold up one with the other by supporting plates 40 and 41 placed at their upper and lower ends.

The Peltier effect module 35 is pasted on the surface 1 by means of a fixing agent 2a conducting heat.

In FIG. 6a, the current I direction is like the upper plate 40, that is used as a sensitive element in the invention meaning, and is cooling down as indicated by the arrows 42 that materialize the heat flow.

Conversely, the arrows 43 on the FIG. 6b represent the heat amount transfer towards the said upper plate 40, the current I direction being inverted compared to FIG. 5a.

The electronic circuit 36 allows to invert the supply power direction of the Peltier effect module each time the upper plate 40 of this module presents, compared with the surface 1, a given temperature difference.

Figure 5:
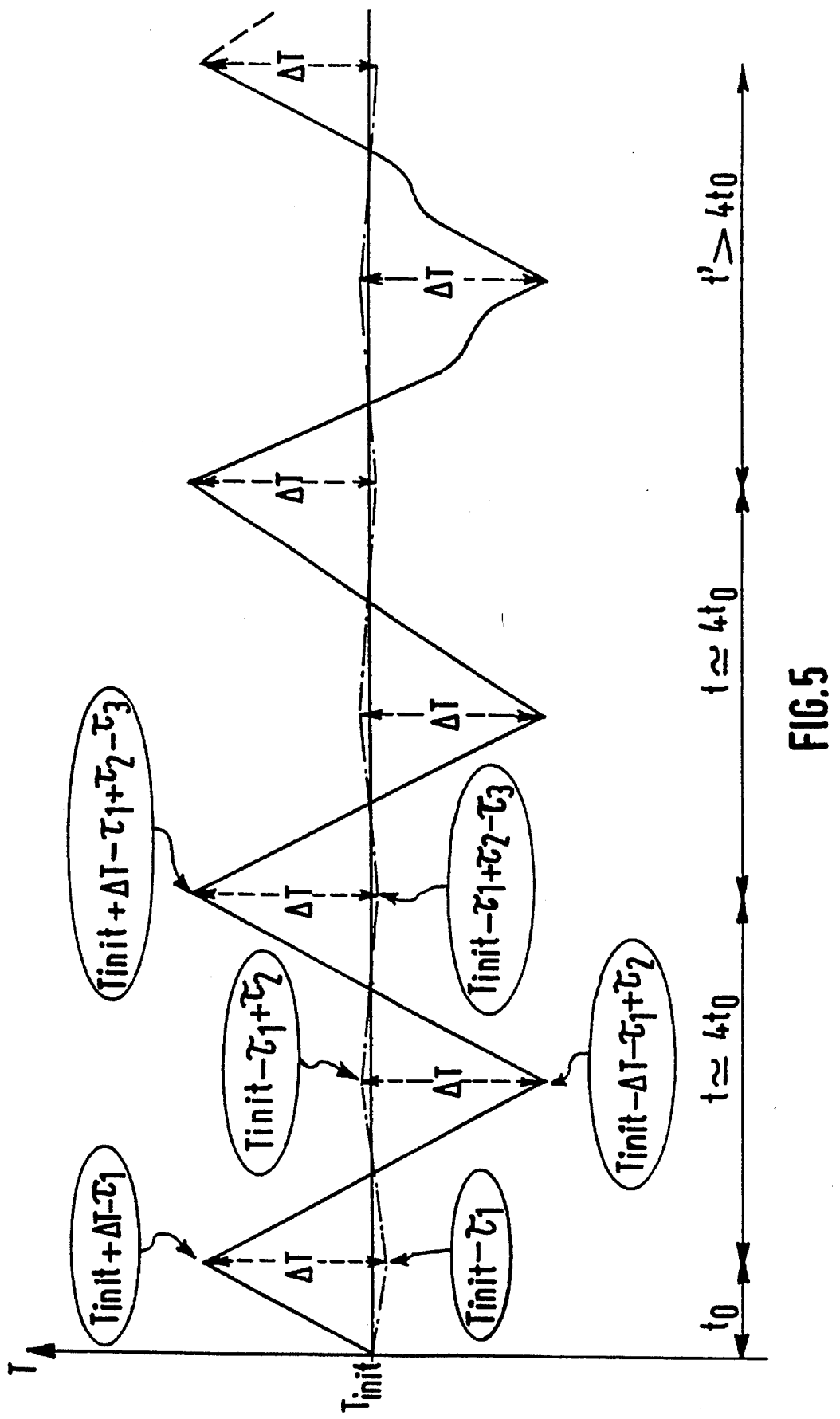
FIG. 5 shows temperature change over time of the sensitive element during the second implementation mode.

FIG. 5 represents the temperature changes of the upper plate 40 (in continuous lines) and those of surface 1 (in mixed lines) during the successive cycles.

Because there is the Peltier effect module 35, the temperature changes of the upper plate 40 can be evaluated without direct measurement of the temperature, by measuring the voltage at the terminals of the Peltier effect module 35, after subtracting the resistive component of this voltage, as will be explained with reference to FIGS. 7 and 8.

This device allows to implement the variant of the invention according to which the duration of a first heating phase is measured and this duration is compared to one quarter of the total duration of successive cycles, each including a cooling phase and a second heating phase.

Thermal amplitude of thermal oscillations is roughly of 2 $\Delta T$.

In this implementation of the invention, no absolute temperature is measured, but only temperature variations between the upper plate 40, which is used as a sensitive element, and the surface 1.

The Peltier effect module 35 helps to continuously perform these measurements, from the voltage signal at this module's terminals.

During the first heating phase, a current I circulates through the Peltier effect module, the upper plate 40 is heated while the surface 1 is cooled down.

Taking into account the important differences of the thermal time constant between the surface 1 and the upper plate 40, the said plate reaches s, $Tinit+\Delta T-\Gamma_1$ temperature, $\Gamma_1$ being very small compared to $\Delta T$, while the surface 1 reaches a temperature of $Tinit-\Gamma_1$.

The voltage at the terminals of the Peltier effect module does not allow to measure the absolute temperature of the upper plate 40, but allows to detect that the temperature difference between upper plate 40 and surface 1 is equivalent to $\Delta T$.

The duration of this first heating phase is recorded.

Then the direction of current I is inverted, in order to provoke the cooling of upper plate 40. The surface 1 then undergoes a slight $\Gamma_2$ heating, $\Gamma_2$ being very small compared to $\Delta T$.

The voltage at the terminals of the Peltier effect module allows to detect the time when the temperature difference between the upper plate 40 and the surface 1 again reaches $\Delta T$, that is to say when the upper plate 40 temperature is equivalent to $Tinit-\Delta T-\Gamma_1+\Gamma_2$, while the surface 1 temperature is equivalent to $-\Gamma_1+\Gamma_2$.

Then a second heating of plate 40 is provoked, in the same way as before, in order to bring it back to a $Tinit+\Delta T-\Gamma_1+\Gamma_2-\Gamma_3$ temperature, $\Gamma_3$ being very small compared to $\Delta T$ and the surface back to the $Tinit-\Gamma_1+\Gamma_2-\Gamma_3$ temperature.

The system is preferably designed so that $-\Gamma_1+\Gamma_2-\Gamma_3$, which is representing the system's temperature drift, is the smallest as possible.

At last the total duration t of the cycle made by the cooling phase and the second heating phase is compared to the quadruple of the duration to of the first heating phase, to conclude or not that there is a condensation risk, like in the previous case.

On the FIG. 5, two cycles without a change of state and with a duration t almost equivalent to $4 t_0$, and a cycle with a change of state and a duration t' superior to $4 t_0$, are represented.

If there is no condensation risk, a new cycle is performed, and its duration t will be compared to the quadruple of the duration $t_0$ of the same first heating phase.

At regular intervals, for instance every 30 cycles, the cycles performance is interrupted to let the surface and the sensitive element reach again a stable temperature according to the environmental conditions, in order to cancel the temperature drift.

Then a new heating of the upper plate is provoked before starting again the cycles succession.

Figure 7:
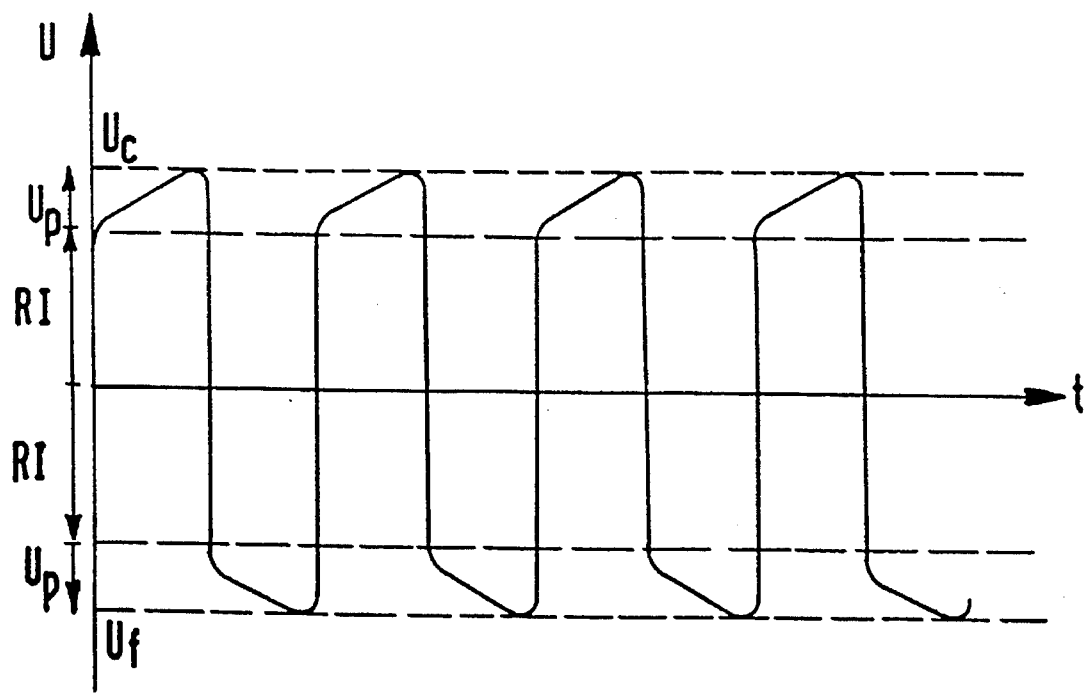
FIG. 7 shows the voltage at the terminals of the device in FIGS. 6a and 6b.

In FIG. 7 there is a diagram of the variations according to the U voltage time at the terminals of the Peltier effect module 35.

The U voltage is composed by a resistive component UR=RI and a Seebeck Up component.

Figure 8:
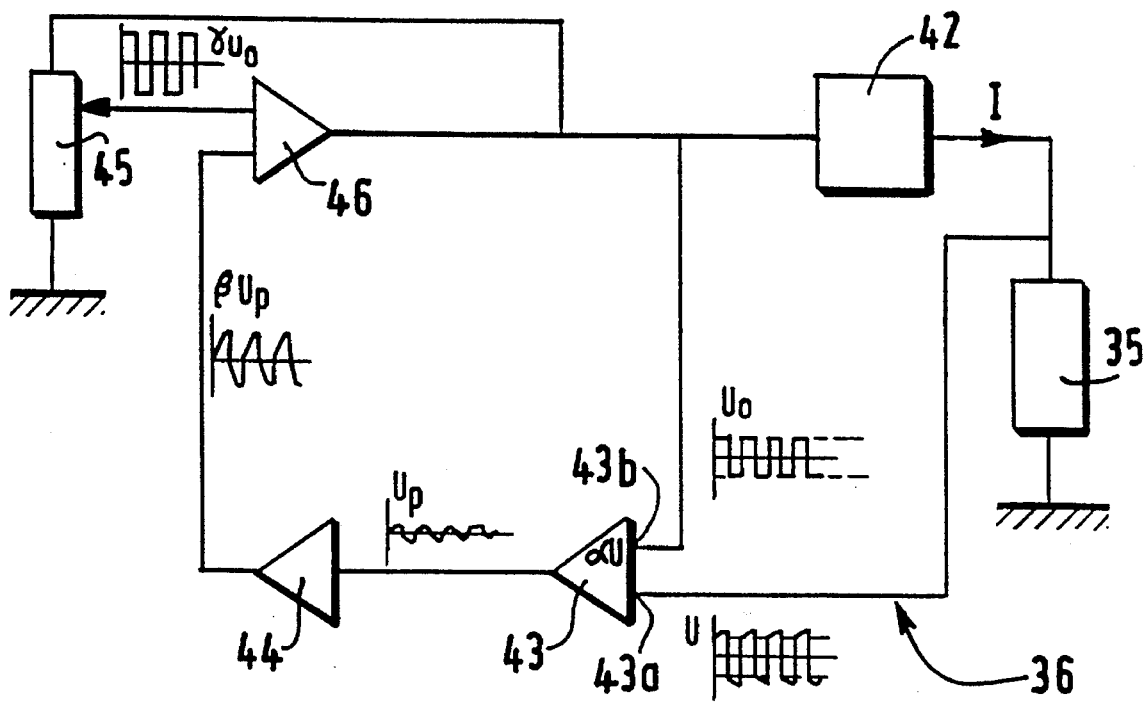
FIG. 8 shows an electronic circuit for the device of FIGS. 6a and 6b.

The electronic circuit 36, which is schematically represented in FIG. 8, determines the moment when the voltage Up reaches the Uc or Uf value, according to the direction of current I flowing in the Peltier effect module 35.

The circuit 36 includes a power generator 42 connected to the Peltier effect module, a subtracter 43, an amplifier 44, a potentiometer 45, and a comparator 46.

The 43, 44 and 46 elements can be concretely realized by operational amplifiers.

For each terminal of an element of circuit 36, the voltage signal present at this terminal was represented.

The operation of circuit 36 will be described from now on.

The power generator 42 sends a current I to the Peltier effect module 35.

The voltage at the module's terminals applied to the terminal 43a of the subtracter 43 is recalled by the diagram U.

The subtracter 43 clears the resistive component of the U signal by subtracting from it the square signal Uo applied to its terminal 43b, the gain of the operational amplifier 43 being such that the amplitude of the Uo signal is brought to the value $\alpha Uo=RI$ prior to be subtracted from U signal.

At the output of subtracter 43, the obtained voltage is Up, Seebeck component of the Peltier effect module voltage.

The amplifier 44 increases the amplitude of the Up signal to provide a $\beta Up$ signal.

The potentiometer 45 also sets the amplitude of signal Uo to provide a $\delta Uo$ signal, the amplitude of which from $-Uc$ to $+Uf$, is corresponding to a Seebeck voltage at the terminals of the Peltier effect module which is obtained when the temperatures variation between the upper plate 40 and the surface 1 is equivalent to $\Delta T$.

Uc and Uf are the voltage thresholds from which the I current direction must be inverted.

The voltage at output terminal of the comparator 46 flips every time that $\beta Up$ voltage exceeds the threshold set by the $\delta Uo$ signal.

Thus we get a self-oscillation of circuit 36 and an alternation of the heating and cooling phases for the Peltier effect module, without making any temperature measurement in order to determine the peaks of the thermal oscillations.

Figure 9:
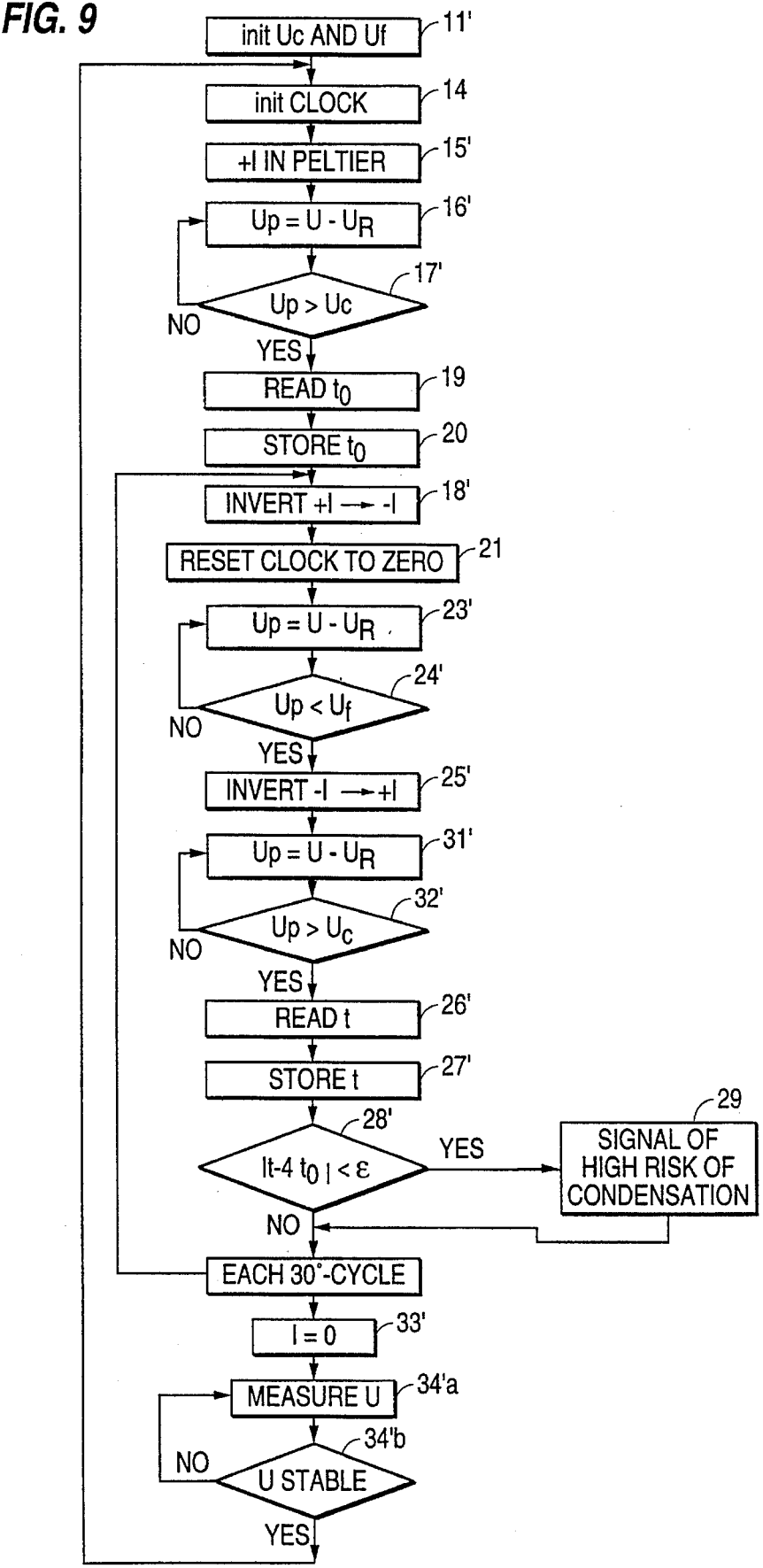
FIG. 9 shows the steps of the second implementation mode of the process of the present invention.

The different steps of the process implemented by using the device of FIGS. 6a and 6b are represented in FIG. 9 in which the same reference numbers have been kept for the steps already described in reference on the FIG. 4.

During a first step 11', the limit voltages Uc and Uf, corresponding to a ΔT temperature gap between the two extremity faces of the Peltier effect module 35, are preset.

A clock is initialized during the following step 14.

At step 15', the heating of the upper plate 40 is started by sending a +I current in the Peltier effect module.

The steps 16' and 17' constitute a waiting loop until the temperature gap between the upper plate 40 and the surface 1 is equivalent to DT, that is to say until the Seebeck voltage at the Peltier effect module terminals is higher than the Uc threshold voltage.

At steps 19 and 20, the to duration of this first heating phase is read and stored.

The thermal oscillation cycle starts at step 18', at which the current I is inverted to start the upper plate 40 cooling.

The clock is reset to zero at step 21.

The steps 23' and 24' constitute a waiting loop until the temperature gap between the upper plate 40 and the surface 1 is again equivalent to ΔT, that is to say until the Seebeck voltage at the Peltier effect module terminals is less than the Uf threshold voltage.

The steps 25', 31' and 32' realize the second heating phase which is happening in a way similar to that of the cooling phase.

At the 26' and 27' steps, the t time of the cycle thus realized is read and stored.

At step 28', the t cycle time is compared to the quadruple of the first heating phase time $t_0$. In case of a difference between these two times, the conclusion is that there is a condensation risk on the surface 1.

Then again a cycle is started from the step 18'.

This process leading almost inevitably to a system temperature drift, it is better to make a pause at regular intervals so that the surface and the sensitive element can reach a stable temperature according to the environmental conditions. To that purpose, the current passage is interrupted during a step 33' and during steps 34'a and 35'b, we wait until the U voltage at the Peltier effect module terminals is stabilized, which means that the system temperature has reached again a stable value according to the environmental conditions, afterwards the process is resumed from the step 14.

We can notice that the power supply currents +I and −I here described can eventually show different absolute values, the heating voltage Ic being less than the cooling voltage If, in order to compensate for the release of the thermal energy produced by Joule effect in the Peltier effect module.

In the other embodiment, where the first heating phase is compared, not to the cooling phase, but to the second heating phase, a same current I can be used to supply the Peltier effect module 35 and its heating thermal power can then be different from the cooling thermal power.

Once the first cycle has thus been identified as causing no change of state, it is possible to compare its duration to that of the subsequent cycles.

Of course it is understood that the embodiments which we just described are not restrictive and that they may undergo any desirable modification without going out of the invention frame.

I claim:

1. A process for detecting risk of water condensation on a surface in contact with a volume of wet air, comprising the steps of:
   (a) placing a sensitive element on the surface causing the element to take on a temperature corresponding to the surface's temperature,
   (b) heating the sensitive element during a first heating phase with a heating device until a temperature higher than the surface's temperature is reached,
   (c) recording time duration and increase in temperature of the element during the first heating phase,
   (d) cooling the sensitive element during a cooling phase with a cooling device having the same thermal capacity as the heating device until a temperature lower than the surface's temperature is reached,
   (e) recording time duration and decrease in temperature of the element during the cooling phase,
   (f) comparing (1) the ratio of the first heating phase time duration to the temperature increase during the first heating phase to (2) the ratio of the cooling phase time duration to the temperature decrease during the cooling phase, wherein a difference between the ratios (1) and (2) corresponds to a risk of condensation on the surface.

2. The process as claimed in claim 1, wherein a predetermined temperature change for the first heating phase is used and the temperature of the element at the end of the cooling phase is set by subtracting the predetermined temperature change from the surface's initial temperature, so that said comparing step (f) only needs to compare the time duration of the first heating phase to half the time duration of the cooling phase to determine the risk of condensation on the surface.

3. The process as claimed in claim 2, further comprising, after the recording step (e), heating the element during a second heating phase with the heating device until the temperature of the element returns to the surface's temperature before the first heating phase and recording time duration of the second heating phase.

4. The process as claimed in claim 3, wherein said comparing step (f) only needs to compare the time duration of the first heating phase to a quarter of the total time duration of a cycle constituting the cooling phase time duration plus the second heating phase time duration to determine the risk of condensation on the surface.

5. The process as claimed in claim 3, wherein said comparing step (f) only needs to compare the time duration of the first heating phase to the time duration of the second heating phase to determine the risk of condensation on the surface.

6. The process as claimed in claim 3, wherein said comparing step (f) only needs to compare the time duration of the cycle constituting the cooling phase time duration plus the second heating phase time duration to a successive cycle constituting a second cooling phase time duration plus a third heating phase time duration to determine the risk of condensation on the surface.

7. The process as claimed in claim 1, wherein a Peltier effect module is used as the sensitive element, the heating device, and the cooling device; and the temperature increase and temperature decrease are recorded by measuring the Seebeck component of voltage at the terminals of the Peltier effect module.

8. The process as claimed in claim 7, wherein the Seebeck component is obtained by eliminating a constant component representative of voltage due to internal resistance of the Peltier effect module at constant temperature.

9. The process as claimed in claim 7, wherein the Seebeck component is obtained by eliminating a variable component due to the internal resistance of the Peltier effect module at the average temperature of the module in the voltage at the terminals of the module.

10. A device for detecting risk of water condensation on a surface in contact with a volume of wet air comprising (a) a sensitive element which, when contacted with the surface, takes on a temperature corresponding to the surface's temperature, (b) a heating device for heating the sensitive element during a first heating phase, (c) means for recording time duration and increase in temperature of the element during the first heating phase, (d) a cooling device for cooling the sensitive element during a cooling phase, (e) means for recording time duration and decrease in temperature of the element during the cooling phase, (f) a control unit for controlling the heating and cooling devices so that the element is first heated to a predetermined temperature above the surface's temperature and then cooled to a temperature below the surface's temperature, and (g) means for comparing (1) the ratio of the first heating phase time duration to the temperature increase during the first heating phase to (2) the ratio of the cooling phase time duration to the temperature decrease during the cooling phase, wherein a difference between the ratios (1) and (2) corresponds to a risk of condensation on the surface.

11. The device as claimed in claim 10, wherein (a), (b) and (d) are a Peltier effect module powered by an electronic circuit that inverts current direction whenever the Seebeck component of voltage at the Peltier effect module terminals exceeds a predetermined value.

* * * * *